(12) United States Patent
Inamoto et al.

(10) Patent No.: US 8,183,232 B2
(45) Date of Patent: May 22, 2012

(54) THERAPEUTIC AGENT FOR HEMORRHOIDAL DISEASE

(75) Inventors: Yukiko Inamoto, Kagawa-gun (JP); Seiichiro Kawabata, Higashikagawa (JP); Mitsuhiro Kawada, Higashikagawa (JP)

(73) Assignee: Teikoku Seiyaku Co., Ltd., Kagawa-ken (JP)

( * ) Notice: Subject to any disclaimer, the term of this patent is extended or adjusted under 35 U.S.C. 154(b) by 947 days.

(21) Appl. No.: 10/545,910

(22) PCT Filed: Feb. 17, 2004

(86) PCT No.: PCT/JP2004/001701
§ 371 (c)(1),
(2), (4) Date: Aug. 17, 2005

(87) PCT Pub. No.: WO2004/073718
PCT Pub. Date: Sep. 2, 2004

(65) Prior Publication Data
US 2006/0159711 A1    Jul. 20, 2006

(30) Foreign Application Priority Data

Feb. 21, 2003  (JP) ................................ 2003-044384

(51) Int. Cl.
*A61K 31/19* (2006.01)
(52) U.S. Cl. .................................................... 514/165
(58) Field of Classification Search .................. None
See application file for complete search history.

(56) References Cited

U.S. PATENT DOCUMENTS

| | | | | |
|---|---|---|---|---|
| 3,740,420 A | * | 6/1973 | Herschler et al. | 424/45 |
| 4,126,681 A | * | 11/1978 | Reller | 514/163 |
| 4,383,986 A | * | 5/1983 | Dubash et al. | 424/443 |
| 4,613,498 A | * | 9/1986 | Crosby | 424/697 |
| 5,932,230 A | * | 8/1999 | DeGrate | 424/401 |
| 6,210,698 B1 | | 4/2001 | Yamazaki et al. | 424/434 |
| 6,268,355 B1 | * | 7/2001 | Mizobuchi et al. | 514/165 |
| 7,029,663 B1 | * | 4/2006 | Mizobuchi et al. | 424/78.05 |
| 2003/0077308 A1 | * | 4/2003 | Rosen | 424/401 |
| 2003/0125308 A1 | * | 7/2003 | Inamoto et al. | 514/165 |
| 2004/0062778 A1 | * | 4/2004 | Shefer et al. | 424/400 |

FOREIGN PATENT DOCUMENTS

| | | |
|---|---|---|
| AU | 1988/17780 | 12/1989 |
| EP | 1022019 | 7/2000 |
| EP | 1256346 | 11/2002 |
| JP | 63-5018 | 1/1988 |
| JP | 8-245369 | 9/1996 |

OTHER PUBLICATIONS

Thomsen et al., Acta Derm. Venereol., (Jan. 2002) 82(1), 30-35.*
Physicians' Desk Reference, 50th edition (Medical Economics), p. 1896-7; 2408-9.*
Remington's Pharmaceutical Sciences, 15th edition (Mack Publishing Co.), pp. 1547-1549.*
Pope et al., Canadian Journal of Comparative Medical and Veterinary Science, (1966), 30(1), pp. 3-8.*
XP002448309, Abstract of CN 1389241 A, Jan. 8, 2003.
John F. Johanson, M.D., "Evidence-based Approach to the Treatment of Hemorrhoidal Disease", Evidence-based Gastroenterology 2002, vol. 3, No. 1, 2002, pp. 26-31.
Supplementary Partial European Search Report issued Sep. 20, 2007 in the corresponding European application.

* cited by examiner

*Primary Examiner* — Phyllis G. Spivack
(74) *Attorney, Agent, or Firm* — Wenderoth, Lind & Ponack, L.L.P.

(57) ABSTRACT

An external preparation containing acetylsalicylic acid or its pharmaceutically acceptable salt as an active ingredient for treating anal diseases having therapeutic activity on hemorrhoids (internal hemorrhoid, external hemorrhoid), hemorrhoidal disease owing to anal fissure and other anal diseases together with activity on pain and pruritus.

1 Claim, No Drawings

THERAPEUTIC AGENT FOR HEMORRHOIDAL DISEASE

TECHNICAL FIELD

The present invention relates to an external preparation having the therapeutic effect to hemorrhoidal diseases and other anal diseases together with anti-pain and/or anti-pruritic activity at the said lesion, and a method for treating said diseases.

In more detail, in case of treatment of hemorrhoidal diseases and other anal diseases associated with pain and/or pruritus by administering acetylsalicylic acid or its pharmaceutically acceptable salt as an active agent, the present invention relates to the external agent having the therapeutic activity of the lesion together with the activity to alleviate pain and/or pruritus at the lesion, and the method for treating said diseases.

BACKGROUND ART

There are many patients suffering from hemorrhoidal diseases such as hemorrhoids (internal hemorrhoid, external hemorrhoid) and anal fissure, and other anal diseases, and many of these diseases associated with inflammation, severe pain and/or pruritus.

Nowadays as agents for treating hemorrhoidal diseases, a suppository and an ointment containing a local anesthesia, a steroid, an antihistamine, etc. are used, but administration of the local anesthesia or the external steroid often causes to delay of the wound healing and there is a possibility that systemic side effect may occur.

Furthermore, in general as to administer a nonsteroidal antiinflammatory agent to the mucosal injured legion causes to delay of the remedy of said lesion, it is considered to be contraindication.

In regard to therapy of hemorrhoidal diseases and other anal diseases, the preparations in which the drugs having their effects respectively are contained, have been patiently used even if these drugs extend the therapeutic time.

By the way, from of old acetylsalicylic acid (it may be written as aspirin.) has been widely used as an antipyretic analgesic agent mainly in oral administration form as it has potent analgesic activity, antifebrile activity and antirheumatic activity. Aspirin is safe as its side effect is less.

Recently the external application of acetylsalicylic acid has been studied.

Furthermore, as a new use of acetylsalicylic acid in the form of an external preparation, ointments for treating neuralgia (Japanese Patent Publication A3-72426), external preparations for treating skin injury (Japanese Patent Publication A9-235232), a transdermal administration system for treatment of thrombosis and for prophylactic treatment of cancer (Japanese Patent Publication Tokuhyo 8-504198), external preparations for treating allergic dermatitis (Japanese Patent Publication A11-373511) and external preparations for treating pruritus (WO 01/47525) are illustrated.

However, the external preparation containing acetylsalicylic acid in order to treat hemorrhoidal diseases and other anal diseases and in order to restrain pain and/or pruritus associating with their diseases has not been reported.

DISCLOSURE OF INVENTION

The present invention is to dissolve the above problems and its object is to provide an external preparation containing acetylsalicylic acid as an active ingredient which is less in side effect, has excellent therapeutic effect for hemorrhoidal diseases and other anal diseases, and excellent alleviating effect on pain and/or pruritus associated with said anal diseases and that does not delay the remedy on the lesion.

The present invention relates to the external preparation for treating anal diseases containing acetylsalicylic acid or its pharmaceutically acceptable salt as an active ingredient.

The present invention relates to the external preparation for treating internal hemorrhoid, external hemorrhoid, or hemorrhoidal disease owing to anal fissure containing acetylsalicylic acid or its pharmaceutically acceptable salt as an active ingredient.

The present invention relates to the external preparation for treating internal hemorrhoid, external hemorrhoid, or hemorrhoidal disease owing to anal fissure containing in the amount of 0.01 to 20% by weight of acetylsalicylic acid or its pharmaceutically acceptable salt as an active ingredient.

The present invention also relates to the method for treating anal diseases, such as hemorrhoids (internal hemorrhoid, external hemorrhoid), hemorrhoidal disease owing to anal fissure, etc., and for alleviating the pain or pruritus associated with said disease, administering an effect amount of acetylsalicylic acid or its pharmaceutically acceptable salt to the lesion on the patient.

The present inventors have been extensively studied to dissolve the above problems and found that in case of administration of the external preparation containing acetylsalicylic acid as an active ingredient to the patients, said preparation shows less side effect and shows the excellent therapeutic effects on hemorrhoidal diseases and other anal diseases together with alleviating activity on pain and/pruritus at said lesion. Thus the present invention was completed.

BEST MODE FOR CARRYING OUT THE INVENTION

Namely, the external preparation containing acetylsalicylic acid was prepared, and when said preparation was applied to the lesion of the patients, for example to the lesion of hemorrhoidal diseases, such as hemorrhoids (internal hemorrhoid, external hemorrhoid) and anal fissure, and other anal diseases, the excellent therapeutic activity was confirmed and furthermore excellent alleviating activity to pain and/or pruritus on the lesion was confirmed.

This effect depends on the concentration of acetylsalicylic acid in the preparation, but when the concentration is beyond certain amount, the pharmacological effect thereof is almost not changed.

Acetylsalicylic acid contained in the external preparation of the present invention is described in the Pharmacopoeia of Japan XIII.

The amount of acetylsalicylic acid in the external preparation depends on the form of the preparation, but is 0.01-20% by weight, which shows sufficient effect, preferably 0.05-20%, more preferably 0.05-10% per total amount of the preparation. When the amount of acetylsalicylic acid is less than 0.01% by weight, the alleviating effect on pain and therapeutic activity by acetylsalicylic acid does not show enough. When the amount of acetylsalicylic acid is more than 20% by weight, it is impossible to prepare the preparation.

Acetylsalicylic acid contained in the external preparation of the present invention may be used in the form of a pharmaceutically acceptable salt with an amino acid such as DL-lysine or a pharmaceutically acceptable inorganic salt such as a sodium salt, as well as acetylsalicylic acid.

The external preparation of the present invention is not limited as far as it is the preparation in which acetylsalicylic acid can be directly applied on the local surface of skin, such as ointments, patches, solutions (e.g. suspensions, emulsions, lotions), suppositories, cataplasms, tapes, aerosols and so on.

As ingredients of the preparation of the present invention can be used any ingredient used in the ordinarily external preparation.

In case of ointments, creams, gels and lotions, bases, such as white vaseline (petrolatum), yellow vaseline, lanolin, purified bee wax, cetanol, stearyl alcohol, stearic acid, hydrogenated oil, hydrocarbon gel, polyethylene glycol, liquid paraffin and squalane; solvents or solubilizing agents, such as oleic acid, isopropyl myristate, glycerol triisooctanoate, crotamiton, diethyl sebacate, diisopropyl adipate, hexyl laulate, a fatty acid, a fatty acid ester, an aliphatic alcohol and a vegetable oil; antioxidants, such as a tocopherol derivative, L-ascorbic acid, dibutylhydroxytoluene and butylhydroxyanisole; antiseptics such as p-hydroxybenzoate; humectants, such as glycerin, propylene glycol and sodium hyaluronate; surfactants, such as a polyoxyethylene derivative, a glycerol fatty acid ester, a sucrose fatty acid ester, a sorbitan fatty acid ester, a propylene glycol fatty acid ester and lecithin; thickening agents, such as carboxyvinyl polymer, xanthan gum, carboxymethyl cellulose, sodium carboxymethyl cellulose, hydroxypropyl cellulose and hydroxypropylmethyl cellulose; propellants, such as liquid petroleum gas, liquid carbon dioxide, dimethyl ether, nitrogen gas, kerosine, carbon dioxide, etc.; stabilizers; preservatives; absorption enhancers; and other suitable fillers are used.

In case of suppositories, an oily base, an aqueous base or a hydrophylic base is used. The oily base includes hard fat such as cacao butter, semisynthetic oily base. The aqueous or hydrophilic base includes macrogol, agar, gelatin, glycerin, etc. Furthermore, a surfactant, solubilizing agents, antiseptics, emulsifying agents, dispersion agents, auxiliaries and so on may be used.

In case of cataplasms, tackifiers, such as polyacrylic acid and polyacrylic acid copolymer; crosslinkers, such as aluminum sulfate, aluminum potassium sulfate, aluminum chloride, magnesium aluminometasilicate and dihydroxyaluminum iminoacetate; thickening agents, such as sodium polyacrylate, polyvinyl alcohol, polyvinylpyrrolidone, gelatin, sodium alginate, carboxymethyl cellulose, sodium carboxymethyl cellulose, hydroxypropyl cellulose and hydroxypropylmethyl cellulose; polyhydric alcohols, such as glycerin, polyethylene glycol (macrogol), propylene glycol and 1,3-butanediol; surfactants such as a polyoxyethylene derivative; perfumes such as l-menthol; antiseptics such as p-hydroxybenzoate; purified water; and other suitable fillers may be used.

In case of tapes, tacking agents, such as a styrene-isoprene-styrene block copolymer and an acrylate resin; tackifier resins, such as an alicyclic saturated hydrocarbon resin, a hydrogenated rosin resin and a terpene resin; softeners, such as liquid gum and liquid paraffin; antioxidants such as dibutylhydroxytoluene; polyhydric alcohols such as propylene glycol; absorption enhancers such as oleic acid; surfactants such as a polyoxyethylene derivative; and other suitable fillers may be used. In addition a water-absorbing polymer, such as sodium polyacrylate and polyvinyl alcohol, and a small amount of purified water may be added to prepare tape preparations containing water.

In case of aerosols, bases, such as white vaseline (petrolatum), yellow vaseline, lanolin, purified bee wax, cetanol, stearyl alcohol, stearic acid, hydrogenated oil, hydrocarbon gel, polyethylene glycol, liquid paraffin and squalane; solvents or solubilizing agents, such as oleic acid, isopropyl myristate, isopropyl adipate, isopropyl sebacate, glycerol triisooctanoate, crotamiton, diethyl sebacate, hexyl laurate, a fatty acid, a fatty acid ester, an aliphatic alcohol and a vegetable oil; antioxidants, such as a tocopherol derivative, L-ascorbic acid, dibutylhydroxytoluene and butylhydroxyanisole; antiseptics such as p-hydroxybenzoate; humectants, such as glycerin, propylene glycol and sodium hyaluronate; surfactants, such as a polyoxyethylene derivative, a glycerol fatty acid ester, a sucrose fatty acid ester, a sorbitan fatty acid ester, a propylene glycol fatty acid ester and lecithin; thickening agents, such as carboxyvinyl polymer, xanthan gum, carboxymethyl cellulose, sodium carboxymethyl cellulose, hydroxypropyl cellulose and hydroxypropylmethyl cellulose, as used in the above mentioned ointments, creams, gels, suspensions, emulsifying agents or lotions; fillers, such as potato starch, rice starch, corn starch, talc and zinc oxide; propellants such as liquid petroleum gas, liquid carbon dioxide, dimethyl ether, nitrogen gas, kerosine and carbon dioxide; stabilizers; buffering agents; sweetening agents; suspending agents; emulsifying agents; flavors; preservatives; solubilizing agents; and other suitable fillers may be used.

The external preparation of the present invention is prepared by the method in accordance with a conventional method for preparing the external preparations such as by well kneading each ingredient and if necessary, a suitable base. Thus prepared preparation is applied in accordance with a conventional method for example, by being directly applied to the lesion or applied it after spreading on cloth or immersing it in cloth.

The ointments are prepared as follows: By using, as a starting material, fat, a fatty oil, lanolin, wax, resin, plastics, glycol, a high molecular weight alcohol, glycerin, water, an emulsifying agent, a suspension agent or a suitable additive, or by using these substances as a base, the drug is added thereto and the mixture is blended to be completely homogenous to prepare ointments.

After the base is melted under warming and homogenously stirred and if necessary, thereto are added additives such as an absorption enhancer, an antioxidant, an antiseptic, a surfactant, purified water, etc. To the mixture were added under stirring acetylsalicylic acid in powders to prepare ointments or creams.

The suppositories are prepared as follows: By using an oily base, a hydrous base, or a suitable substance as a base and after melting it under warming, the active ingredient itself, or if necessary, an emulsifying agent or a suspending agent is added thereto, and the mixture is homogeneously kneaded. The mixture is formed and enclosed or wrapped with a suitable coating to prepare suppositories.

The cataplasms are prepared as follows: After previously mixing the drug with an ointment base containing mainly a water soluble polymer rich in water preservative, such as gelatin, carmellose sodium, methyl cellulose, sodium polyacrylate, etc., the mixture is spread on a support such as unwoven cloth, etc. The surface of the base is covered with a plastic film such as polyethylene, polypropylene, etc., and if necessary, it is cut in desired size.

The tapes are prepared as follows: By adding to an adhesive agent such as styrene-isoprene-styrene block copolymer, acryl resin, etc., a tackifier such as alicyclic saturated hydrocarbon resin, rosin resin, terpene resin, a softener such as liquid gum, liquid paraffin, etc., an absorption enhancer, an antioxidant, etc., the mixture is dissolved in an organic solvent such as toluene or the mixture was melted under heating. To the mixture was added the drug in powders or dissolved in a solvent to prepare the mixture. The mixture is spread on release paper, and in case of a solution type, after spreading and drying, it is laminated with a soft support such as a polyurethane film, a polyethylene film, a polyvinyl chloride film, cloth, unwoven cloth, etc. and it is cut in desired size.

The lotions are prepared as follows: After adding the drug, a solvent, an emulsifying agent, a suspension agent, etc., to an aqueous solution, the mixture is homogenously stirred. The suspension-type lotions are prepared as follows: After pulverizing, the drug is treated with glycerin or ethanol, etc., to wet with water, and thereto is gradually added a solution of a suspension agent or a lotion base. The mixture was stirred to be homologous. On the other hand, the emulsion type lotion is prepared as follows: The drug soluble in an oil and an oil phase are put in a vessel. A water phase is put in another vessel. Each vessel is warmed and in case of O/W type emulsion, the oil phase is gradually added to the water phase and in case of W/O the water phase is gradually added to the oil phase on the contrary, and the mixture was stirred until the emulsification is completed to become homogenous.

The aerosols is prepared by preparing a solution containing the drug, an ointment, a cream, a gel, a suspension, an emulsion, a solution, a lotion, etc., in accordance with the above mentioned methods, and by filling it with liquid gas, pressured gas, etc. into a sealed vessel.

The diseases which are directed to the external preparation of the present invention include hemorrhoidal diseases such as hemorrhoid (internal hemorrhoid, external hemorrhoid), anal fissure, etc., and other anal diseases.

The external preparation containing acetylsalicylic acid of the present invention is explained by illustrating examples and test examples, but the present invention should not be limited by these examples.

EXAMPLE

Examples 1 to 7

Ointments

According to the ingredients indicated in Table 1, a base and a solvent were mixed and thereto was added acetylsalicylic acid. The mixture was well kneaded to give ointments, respectively.

TABLE 1

| Ingredient | Example No. | | | | | | |
|---|---|---|---|---|---|---|---|
| | 1 | 2 | 3 | 4 | 5 | 6 | 7 |
| | Ratio (% by weight) | | | | | | |
| Acetylsalicylic acid | 0.2 | 2.0 | 10.0 | 0.1 | 0.5 | 5.0 | 5.0 |
| Crotamiton | | | | 2.0 | | | 2.0 |
| Tween 80 | | | | | 2.0 | 2.0 | |
| Sesame oil | | | 5.0 | | | | |
| Diisopropyl adipate | | 5.0 | | | | | 2.0 |
| Isopropyl myristate | 5.0 | | | | | | |
| White petrolatum | | | | 97.9 | 97.5 | 93 | 91 |
| Hydrocarbon gel | 94.8 | 93.0 | 85.0 | | | | |

Example 8

Solutions

According to the ingredients indicated in Table 2, acetylsalicylic acid was added to a solvent to dissolve or disperse it. Other ingredients were dissolved in purified water under heating and then under vigorously agitating the solution the former solution or dispersed solution was added thereto. The mixture was stirred until it became completely homologous to give solutions.

TABLE 2

| Ingredient | Example 8 Ratio (% by weight) |
|---|---|
| Acetylsalicylic acid | 0.5 |
| Crotamiton | 1.0 |
| Squalane | 3.0 |
| Cetanol | 3.0 |
| Sorbitan sesquioleate | 0.5 |
| Polyoxy(20)cetyl ether | 1.5 |
| Propylene glycol | 5.0 |
| Triethanolamine | 0.4 |
| Purified water | 85.1 |

Examples 9 and 10

Gels

According to the ingredient indicated in Table 3, after melting the aqueous polymer under warming, acetylsalicylic acid was dissolved or dispersed thereto and then thereto was added residual base. The mixture was kneaded until it became completely homogenous to give gels.

TABLE 3

| Ingredient | Example | |
|---|---|---|
| | 9 | 10 |
| | Ratio (% by weight) | |
| Acetylsalicylic acid | 0.1 | 5.0 |
| Crotamiton | 5.0 | |
| Isopropanol | | 5.0 |
| Propylene glycol | 45.0 | 45.0 |
| Polyacrylic acid | 25.0 | 25.0 |
| Triethanolamine | 0.7 | 0.7 |
| Purified water | 24.2 | 19.3 |

Examples 11 and 12

Creams

According to the ingredients indicated in Table 4, after a solid base was dissolved on a water bath, acetylsalicylic acid dissolved or dispersed in a solvent was added thereto. A water-soluble base was dissolved in water and its warmed solution was added to the mixture. The mixture was kneaded until it became completely homogenous to prepare creams.

TABLE 4

| Ingredient | Example | |
|---|---|---|
| | 11 | 12 |
| | Ratio (% by weight) | |
| Acetylsalicylic acid | 0.2 | 2.0 |
| Crotamiton | 2.5 | |
| Sesame oil | | 5.0 |
| Diisopropyl sebacate | 2.5 | |
| Cetanol | 9.0 | 9.0 |
| White petrolatum | 8.0 | 8.0 |
| Hexyldecanol | 1.0 | 1.0 |
| Polyethylene glycol monostrearate | 2.0 | 2.0 |
| Polyoxy(9)lauryl ether | 2.8 | 2.8 |
| Polyoxyethylene(23)cetyl ether | 2.0 | 2.0 |
| Propylene glycol | 12.0 | 12.0 |
| Methylparaben | 0.1 | 0.1 |

TABLE 4-continued

|  | Example | |
| --- | --- | --- |
|  | 11 | 12 |
| Ingredient | Ratio (% by weight) | |
| Propylparaben | 0.1 | 0.1 |
| Purified water | 57.8 | 56.0 |

Example 13

Cataplasms

According to the ingredients indicated in Table 5, a tackifier such as a polyacrylic acid etc. and a thickening agent were dissolved under heating in a polyhydric alcohol such as glycerin, etc. After being cooled, acetylsalicylic acid and other fillers were blended thereto to be homogenous and thereto was added a crosslinker to prepare an adhesive gel base. The gel base was spread on a suitable support such as unwoven fabric to be cut in desired size to prepare cataplasms.

TABLE 5

| Ingredient | Example 13<br>Ratio (% by weight) |
| --- | --- |
| Acetylsalicylic acid | 5.0 |
| Polyacrylic acid | 8.0 |
| Sodium polyacrylate | 4.0 |
| Sodium carboxymethylcellulose | 5.0 |
| Tartaric acid | 1.6 |
| Dihydroxyaluminum aminoacetate | 0.07 |
| Glycerin | 30.0 |
| Crotamiton | 2.0 |
| Castor oil | 1.0 |
| Purified water | 43.33 |

Comparative Examples 1 and 2

As comparative examples, commercialized preparations a and b (Agents for hemorrhoidal disease) shown in Table 6 were used.

TABLE 6

Ingredients of preparations (ointments) of comparative examples

| Comp. ex. | Commercialized ointment | Main ingredient (% by weight) |
| --- | --- | --- |
| 1 | a | Lidocaine (3.0)<br>Diphenhydramine (0.5)<br>Naphazoline hydrochloride (0.02)<br>Allantoin (1.0) |
| 2 | b | Hydrocortisone acetate (0.5)<br>Lidocaine (3.0)<br>Allantoin (1.0)<br>Tetrahydrozoline hydrochloride (0.05))<br>Chlorohexidine hydrochloride (0.25)<br>Tocopherol acetate (3.0)<br>Chlorpheniramine maleate (0.2) |

Test

The effect of the external preparation of the present invention was tested on the patients (volunteers) suffering from hemorrhoidal diseases and other anal diseases.

Test 1 The improvement factor on pain or pruritus on the patients (volunteers) suffering from hemorrhoidal diseases and other anal diseases To 20 patients (volunteers) suffering from anal fissure, internal hemorrhoid, external hemorrhoid or anal pruritus associated with pain or pruritus, was administered the external preparation of acetylsalicylic acid and the improvement factor on pain or pruritus was evaluated.

The improvement factor on pain or pruritus was evaluated based on the following five steps standard:

A: Remarkably effective,
B: Effective,
C: Slightly effective,
D: No change,
E: Worse.

Being slightly effective (C) or more than slightly effective (A, B), the factor was judged to be effective, and its effective rate was calculated.

The result is shown in Table 7.

TABLE 7

The improvement on factor pain or pruritus (subjective symptom) on the patient suffering from hemorrhoidal disease and other anal disease

| Group | Drug (% by weight) | No. of Patient | Evaluation | | | | | Effective rate (%) |
| --- | --- | --- | --- | --- | --- | --- | --- | --- |
|  |  |  | A | B | C | D | E |  |
| Ointment base | — | 3 | 0 | 0 | 0 | 3 | 0 | 0 |
| Example 2 | Acetylsalicylic acid 2.0 | 6 | 5 | 1 | 0 | 0 | 0 | 100 |
| Example 8 | Acetylsalicylic acid 0.5 | 5 | 3 | 1 | 1 | 0 | 0 | 100 |
| Comp. ex. 1 | Lidocaine 3.0, etc. | 6 | 1 | 1 | 2 | 2 | 0 | 67 |

From the result shown in Table 7, it was confirmed that the external preparation of acetylsalicylic acid (Examples 2 and 8) more strongly controlled (restrained) pain or pruritus of patient suffering from hemorrhoidal diseases and other anal diseases comparing with the commercialized ointment a.

Test 2 The improvement factor by objective symptom on the patient suffering from hemorrhoidal disease and other anal disease To 22 patients (volunteers) suffering from anal fissure, internal hemorrhoid, external hemorrhoid or anal pruritus was administered the external preparation of acetylsalicylic acid and the improvement factor on objective symptom was evaluated.

The improvement factor on objective symptom was evaluated based on the following five step-standard:

A: Remarkably effective,
B: Effective,
C: Slightly effective,
D: No change,
E: Worse.

Being slightly effective (C) or more than slightly effective (A, B), the factor was judged to be effective, and its effective rate was calculated.

The result is shown in Table 8.

Table 8

The improvement factor by objective symptom on the patients suffering from hemorrhoidal disease and other anal disease

TABLE 8

The improvement factor on pain or pruritus (objective symptom) on the patients suffering from hemorrhoidal disease and other anal disease

| Group | Drug (% by weight) | No. of patient | A | B | C | D | E | Effective rate (%) |
|---|---|---|---|---|---|---|---|---|
| Ointment base | — | 3 | 0 | 0 | 1 | 1 | 1 | 33 |
| Example 5 | Acetylsalicylic acid 0.5 | 6 | 2 | 2 | 1 | 1 | 0 | 83 |
| Example 12 | Acetylsalicylic acid 2.0 | 6 | 1 | 1 | 2 | 1 | 1 | 67 |
| Comp. ex. 2 | Allantoin 1.0, etc. | 7 | 2 | 1 | 2 | 1 | 1 | 71 |

From the result shown in Table 8, it was confirmed that the external preparation of acetylsalicylic acid (Examples 5 and 12) improved equally or more on objective syndrome of patient suffering from hemorrhoidal diseases or other anal diseases comparing with the commercialized ointment b.

INDUSTRIAL APPLICABILITY

The present invention, can provide the external preparation having excellent effect on hemorrhoidal disease, such as hemorrhoids (internal hemorrhoid, external hemorrhoid) and anal fissure, and anal dermatitis-eczema, periproctic dermal pruritus, rectal mucosal prolapse syndrome, etc. by containing acetylsalicylic acid or its pharmaceutically acceptable salt as an active ingredient in the preparation.

The invention claimed is:

1. A method for treating an anal disease selected from the group consisting of internal hemorrhoid, external hemorrhoid, internal hemorrhoid accompanied by pain or pruritus, and external hemorrhoid accompanied by pain or pruritus, which consists of externally administering an effective amount of acetylsalicylic acid or its pharmaceutically acceptable salt, together with a pharmaceutically acceptable carrier, to a lesion associated with the disease on a patient, wherein the pharmaceutically acceptable carrier is selected from the group consisting of white vaseline, yellow vaseline, lanolin, purified bee wax, cetanol, stearyl alcohol, stearic acid, hydrogenated oil, hydrocarbon gel, polyethylene glycol, liquid paraffin, squalane, oleic acid, isopropyl myristate, glycerol triisooctanoate, crotamiton, diethyl sebacate, diisopropyl adipate, hexyl laurate, a fatty acid, a fatty acid ester, an aliphatic alcohol, vegetable oil, tocopherol, L-ascorbic acid, dibutylhydroxytoluene, butylhydroxyanisole, p-hydroxybenzoate, glycerin, propylene glycol, sodium hyaluronate, polyoxyethylene, a glycerol fatty acid ester, a sucrose fatty acid ester, a sorbitan fatty acid ester, a propylene glycol fatty acid ester, lecithin, carboxyvinyl polymer, xanthan gum, carboxymethyl cellulose, sodium carboxymethyl cellulose, hydroxypropyl cellulose, hydroxypropylmethyl cellulose, liquid petroleum gas, liquid carbon dioxide, dimethyl ether, nitrogen gas, kerosine, carbon dioxide, cacao butter, macrogol, agar, gelatin, polyacrylic acid, polyacrylic acid copolymer, aluminum sulfate, aluminum potassium sulfate, aluminum chloride, magnesium aluminometasilicate, dihydroxyaluminum aminoacetate, sodium polyacrylate, polyvinyl alcohol, polyvinylpyrrolidone, sodium alginate, carboxymethyl cellulose, sodium carboxymethyl cellulose, 1,3-butanediol, l-menthol, p-hydroxybenzoate, purified water, styrene-isoprene-styrene block copolymer, an acrylate resin, an alicyclic saturated hydrocarbon resin, a hydrogenated rosin resin, a terpene resin, liquid gum, liquid paraffin, isopropyl adipate, isopropyl sebacate, glycerol triisooctanoate, potato starch, rice starch, corn starch, talc, zinc oxide, carmellose sodium, methyl cellulose, alicyclic saturated hydrocarbon resin, rosin resin, and ethanol.

* * * * *